United States Patent

Haley

Patent Number: 5,342,980
Date of Patent: Aug. 30, 1994

[54] FUNGICIDAL AGENTS

[75] Inventor: Gregory J. Haley, Langhorne

[73] Assignee: American Cyanamid Company, Wayne, N.J.

[21] Appl. No.: 998,499

[22] Filed: Dec. 30, 1992

[51] Int. Cl.$^5$ .............................. C07F 1/08
[52] U.S. Cl. .................... 556/117; 562/621; 562/874; 556/117; 556/130; 556/146; 556/182; 560/312; 560/313
[58] Field of Search ............... 560/313, 312; 556/117, 556/130, 146, 182; 562/621, 874; 514/575

[56] References Cited

FOREIGN PATENT DOCUMENTS

92/10469  6/1992  PCT Int'l Appl.

OTHER PUBLICATIONS

Sibi, M. et al Tetrahedron Lett 33(15) 1941–44 1992.
CA 94(17):137790t Japanese Patent Application 79-27,253 filed on Sep. 17, 1980.

Primary Examiner—Paul J. Killos
Attorney, Agent, or Firm—Michael P. Morris

[57] ABSTRACT

There are provided hydroxamic acids, and the esters and chelates thereof having the structure

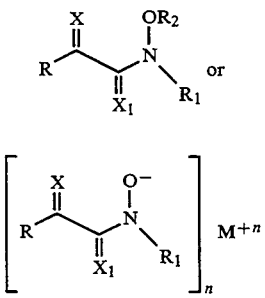

and their use for the prevention, control or amelioration of diseases caused by phytopathogenic fungi. Further provided are compositions and methods comprising those compounds for the protection of plants from fungal infestation and disease.

20 Claims, No Drawings

FUNGICIDAL AGENTS

BACKGROUND OF THE INVENTION

Phytopathogenic fungi are the causal agents for many diseases that infect and destroy crops. In particular, the diseases sugar beet cercospora leaf spot, apple scab, tomato early blight, banana black sigatoka, peanut leaf spot, and grape and pepper botrytis are especially devastating.

Sugar beet is susceptible to many foliar diseases caused by phytopathogenic fungi. One of the most frequently encountered and destructive foliar diseases occurring on sugar beet is sugar beet cercospora leaf spot, caused by the fungus, Cercospora beticola. Sugar beet cercospora leaf spot is common to sugar beet plants throughout the world, and is particularly destructive in regions with wet, warm growing seasons, such as Western and Southern Europe, and the Midwestern United States. During periods of high temperature and wetness, sugar beet cercospora leaf spot spreads rapidly in the field. Ultimately, the disease kills sugar beet leaf tissue, resulting in reduced sugar beet weight and sugar content.

The leaves and fruit of apple trees are susceptible to attack by a fungus, Venturia inaequalis, resulting in a disease called apple scab. The disease occurs wherever apples are grown, but is most common in the United States and Europe. Uncontrolled, apple scab results in deformed, low quality fruit.

Tomatoes are also susceptible to diseases caused by fungi. For example, the foliage, stem and fruit of the tomato plant may be attacked by a fungus, Alternaria solani, resulting in a disease called tomato early blight. Tomato early blight occurs wherever tomatoes are grown, but is particularly destructive in regions with wet or humid climates. Uncontrolled, tomato early blight causes the defoliation of the tomato plant, resulting in reduced fruit number and size.

The leaves of the banana plant are also subject to attack by fungi, for example, Mycosphaerella fijiensis, which causes a disease called banana black sigatoka. Uncontrolled, banana black sigatoka kills the leaves of the banana plant, resulting in small, poor quality fruit. Because bananas are a major export for many Latin American and other tropical countries, the control of banana black sigatoka is critical to those countries' economies.

Currently, only five fungicide classes are used to treat banana black sigatoka. In some areas, the offending fungus has become resistant to the two most effective of those fungicide classes. The result has been more intensive spraying with the less effective fungicides. Therefore, there is a need for new fungicides with other modes of action for the continued protection of bananas.

Peanut leaf spot, caused by fungi of the Mycosphaerella genus, such as Mycosphaerella arachidis, but more importantly fungi such as Cercospora arachidicola and Cercosporidium personatum, is the most destructive foliar disease of peanut plants in the southeastern United States. Uncontrolled, peanut leaf spot causes the rapid defoliation of entire fields, resulting in reduced pod size and number. To date, management of peanut leaf spot has been difficult. Because of the development of resistance to certain fungicides, and the repeal of regulatory approval for other fungicides, ninety-nine percent of the peanuts grown in this region are sprayed with a single fungicide.

Grapes and peppers are susceptible to attack by the fungus, Botrytis cinerea, causing grape botryitis and pepper botrytis, respectively. Grape botrytis, for example, is an especially destructive disease that destroys the cell walls of the fruit, resulting in bunch rot. Grape botrytis occurs wherever grapes are grown, but is most common in Europe.

In spite of the commercial fungicides available today, diseases caused by fungi still abound. Accordingly, there is ongoing research to create new and more effective fungicides for controlling or preventing diseases caused by phytopathic fungi.

It is therefore an object of the present invention to provide compounds which are highly effective for controlling or preventing phytopathogenic fungal infestations in agronomic crops, both growing and harvested.

It is also an object of the present invention to provide a method for the prevention, control or amelioration of a disease caused by a phytopathogenic fungus by contacting said fungus with a fungicidally effective amount of a compound.

These and other objects of the present invention will become more apparent from the detailed description thereof set forth below.

SUMMARY OF THE INVENTION

The present invention describes hydroxamic compounds, the esters and chelates thereof, and their use as fungicidal agents.

The hydroxamic compounds of the present invention have the following structural formula

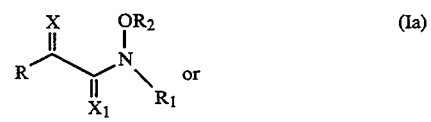 (Ia)

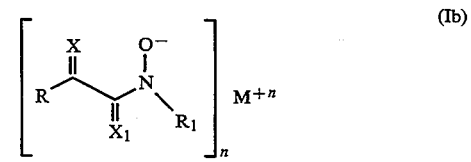 (Ib)

wherein

X and $X_1$ are each independently O or S;

R is $C_1$–$C_6$ alkyl optionally substituted with one or more halogen atoms, or $C_3$–$C_{12}$ cycloalkyl or polycycloalkyl optionally substituted with one or more $C_1$–$C_4$ alkyl groups;

$R_1$ is $C_3$–$C_8$ cycloalkyl, $C_1$–$C_8$ alkyl optionally substituted with one or more halogen atoms, benzyl optionally substituted with one or more halogen, CN, $NO_2$, $C_1$–$C_4$ alkyl $C_1$–$C_4$ haloalkyl groups, or phenyl optionally substituted with one or more halogen, CN, NO$_2$, C$_1$-C$_4$ alkyl or C$_1$-C$_4$ haloalkyl groups;

R$_2$ is hydrogen or

R$_3$ is hydrogen,
OR$_4$,
NR$_5$R$_6$,
C$_1$-C$_6$ alkyl optionally substituted with one or more halogen atoms,
C$_3$-C$_8$ cycloalkyl optionally substituted with one or more halogen atoms,
C$_2$-C$_6$ alkenyl optionally substituted with one or more halogen atoms, or
phenyl optionally substituted with one or more halogen, CN, NO$_2$, C$_1$-C$_4$ alkyl, C$_1$-C$_4$ alkoxy or C$_1$-C$_4$ haloalkyl groups;

R$_4$ is C$_1$-C$_6$ alkyl;
R$_5$ and R$_6$ are each independently hydrogen, C$_1$-C$_6$ alkyl, or
phenyl optionally substituted with one or more halogen, CN, NO$_2$, C$_1$-C$_4$ alkyl or C$_1$-C$_4$ haloalkyl groups;
n is an integer of 1, 2, 3 or 4; and
M is an alkali metal, an alkaline earth metal, a transition metal, boron or aluminum.

This invention also relates to compositions and methods comprising those compounds for the prevention, control or amelioration of diseases caused by phytopathogenic fungi.

DETAILED DESCRIPTION OF THE INVENTION

Phytopathogenic fungi are the causal agents for many diseases that infect and destroy agronomic crops, both growing and harvested. In the United States alone, agronomic crops must compete with about 18,000 species of fungi. Especially devastating are diseases such as sugar beet cercospora leaf spot, apple scab, tomato early blight, banana black sigatoka, peanut leaf spot, grape or pepper botrytis and the like. Accordingly, there is ongoing research to create new and more effective fungicides for preventing or controlling the vast array of fungal infestations of crops.

Advantageously, the present invention provides a method for the prevention, control or amelioration of a disease caused by a phytopathogenic fungus by contacting said fungus with a fungicidally effective amount of a hydroxamic compound of the invention.

The present invention also provides a method for the protection of a plant, plant seed or tuber from fungal infestation and disease by applying to the plant, plant seed or tuber, or to the soil or water in which it is growing, a fungicidally effective amount of a hydroxamic compound of the invention.

Further, the present invention provides hydroxamic compounds which have the following structural formula:

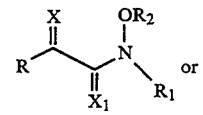

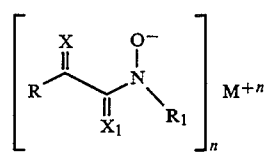

wherein
X and X$_1$ are each independently O or S;
R is C$_1$-C$_6$ alkyl optionally substituted with one or more halogen atoms, or
C$_3$-C$_{12}$ cycloalkyl or polycycloalkyl optionally substituted with one or more C$_1$-C$_4$ alkyl groups;
R$_1$ is C$_3$-C$_8$ cycloalkyl,
C$_1$-C$_8$ alkyl optionally substituted with one or more halogen atoms,
benzyl optionally substituted with one or more halogen, CN, NO$_2$, C$_1$-C$_4$ alkyl or C$_1$-C$_4$ haloalkyl groups, or
phenyl optionally substituted with one or more halogen, CN, NO$_2$, C$_1$-C$_4$ alkyl or C$_1$-C$_4$ haloalkyl groups;
R$_2$ is hydrogen or

R$_3$ is hydrogen,
OR$_4$,
NR$_5$R$_6$,
C$_1$-C$_6$ alkyl optionally substituted with one or more halogen atoms,
C$_3$-C$_8$ cycloalkyl optionally substituted with one or more halogen atoms,
C$_2$-C$_6$ alkenyl optionally substituted with one or more halogen atoms, or
phenyl optionally substituted with one or more halogen, CN, NO$_2$, C$_1$-C$_4$ alkyl, C$_1$-C$_4$ alkoxy or C$_1$-C$_4$ haloalkyl groups;
R$_4$ is C$_1$-C$_6$ alkyl;
R$_5$ and R$_6$ are each independently hydrogen, C$_1$-C$_6$ alkyl, or
phenyl optionally substituted with one or more halogen, CN, NO$_2$, C$_1$-C$_4$ alkyl or C$_1$-C$_4$ haloalkyl groups;
n is an integer of 1, 2, 3 or 4, up to the maximum valence of M; and
M is an alkali metal, an alkaline earth metal, a transition metal, boron or aluminum.

Preferred fungicidal agents of the present invention are oxo- and thiohydroxamic compounds of formula Ia or Ib wherein
X is O;
X$_1$ is S;
R is C$_1$-C$_6$ alkyl;
R$_1$ is C$_1$-C$_8$ alkyl;
R$_2$ is hydrogen or

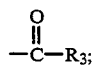

$R_3$ is phenyl optionally substituted with one or more halogen, CN, $NO_2$, $C_1$-$C_4$ alkyl, $C_1$-$C_4$ alkoxy or $C_1$-$C_4$ haloalkyl groups;

n is an integer of 2 or 3; and

M is iron, zinc or copper.

Most preferred fungicidal agents of the present invention are those represented by formula Ib, substituted as described above for the preferred fungicidal agents.

Hydroxamic compounds of the present invention which are particularly effective as fungicidal agents include N,3,3-trimethyl-2-oxo-1-thiobutyrohydroxamic acid iron(+3) chelate;

N,3,3-trimethyl-2-oxo-1-thiobutyrohydroxamic acid copper(+2) chelate;

N,3,3-trimethyl-2-oxo-1-thiobutyrohydroxamic acid zinc(+2) chelate; and p-chlorobenzoate ester of N,3,3-trimethyl-2-oxo-1-thiobutyrohydroxamate, among others.

The term halogen used herein includes fluorine, chlorine, bromine and iodine. The terms alkali metal includes lithium, sodium and potassium, alkaline earth metal includes magnesium, calcium and barium, and transition metal includes iron, zinc, copper, manganese, cobalt, silver, nickel, and the like, preferably iron, zinc and copper. In addition, other elements conventionally understood to be encompassed by the terms halogen, alkali metal, alkaline earth metal and transition metal, are contemplated to be useful in the compounds of the invention. The term polycycloalkyl designates a bicyclic or tricyclic ring system.

The hydroxamic compounds of the present invention are useful in the prevention, control or amelioration of diseases such as sugar beet cercospora leaf spot, apple scab, tomato early blight, banana black sigatoka, peanut leaf spot, and grape or pepper botrytis. Such diseases are caused by, inter alia, the phytopathogenic fungi *Cercospora beticola*, *Venturia inaequalis*, *Alternaria solani*, *Mycosphaerella fijiensis*, *Cercospora arachidicola* and *Botrytis cinerea*, respectively. The compounds of the present invention are especially effective in the prevention, control or amelioration of sugar beet cercospora leaf spot, which can be caused by the fungus, *Cercospora beticola*.

Thiohydroxamic compounds of formula Ia and Ib wherein $R_2$ is hydrogen or $COR_3$ may be prepared as shown in Flow Diagram I.

FLOW DIAGRAM I

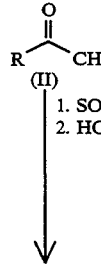

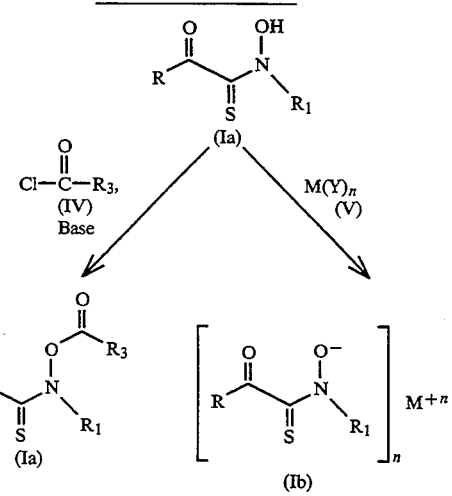

In Flow Diagram I, Y is $OC(O)CH_3$ or Cl and R, $R_1$, $R_3$, M and n as are described above.

As illustrated in Flow Diagram I, the appropriately substituted formula II ketone may be reacted with thionyl chloride in the presence of an organic base such as pyridine to form an intermediate compound which is then reacted with a formula III hydroxylamine (or hydroxylamine hydrohalide salt) in the presence of pyridine to yield the formula Ia compound wherein $R_2$ is hydrogen. The formula Ia compound may then be reacted with an appropriate formula IV acid chloride to obtain those formula Ia compounds wherein $R_2$ is $COR_3$. Alternatively, the formula Ia compound wherein $R_2$ is hydrogen may be reacted with a formula V metal complex to give a chelate of formula Ib.

Compounds of formula Ia and Ib wherein X and $X_1$ are S and $R_2$ is hydrogen or $COR_3$ may be prepared as shown in Flow Diagram II.

FLOW DIAGRAM II

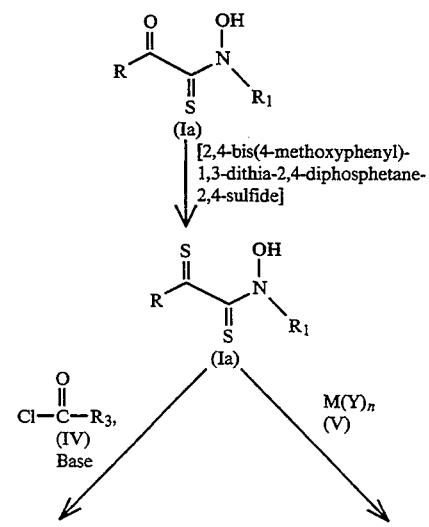

-continued
FLOW DIAGRAM II

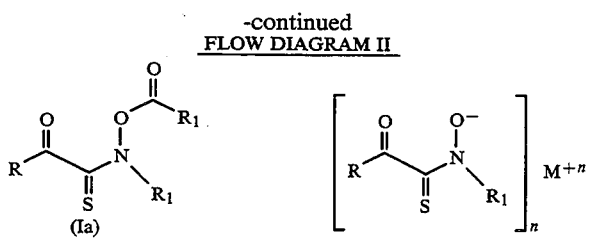

In Flow Diagram II, Y is $OC(O)CH_3$ or Cl and R, $R_1$, $R_3$, M and n are as described above.

As illustrated in Flow Diagram II, the appropriately substituted formula Ia compound wherein X is O, $X_1$ is S and $R_2$ is hydrogen may be reacted with [2,4-bis(4-methoxyphenyl)-1,3-dithia-2,4-diphosphetane-2,4-disulfide] to form the formula Ia compound wherein X and $X_1$ are S and $R_2$ is hydrogen. The formula Ia compound wherein X and $X_1$ are S and $R_2$ is hydrogen may then be reacted with an appropriate formula IV acid chloride to obtain those formula Ia compounds wherein $R_2$ is $COR_3$. Alternatively, the formula Ia compound wherein X and $X_1$ are S and $R_2$ is hydrogen may be reacted with a formula V metal complex to give a chelate of formula Ib.

Hydroxamic compounds of formula Ia and Ib wherein X and $X_1$ are O and $R_2$ is hydrogen or $COR_3$ may be prepared as shown in Flow Diagram III.

FLOW DIAGRAM III

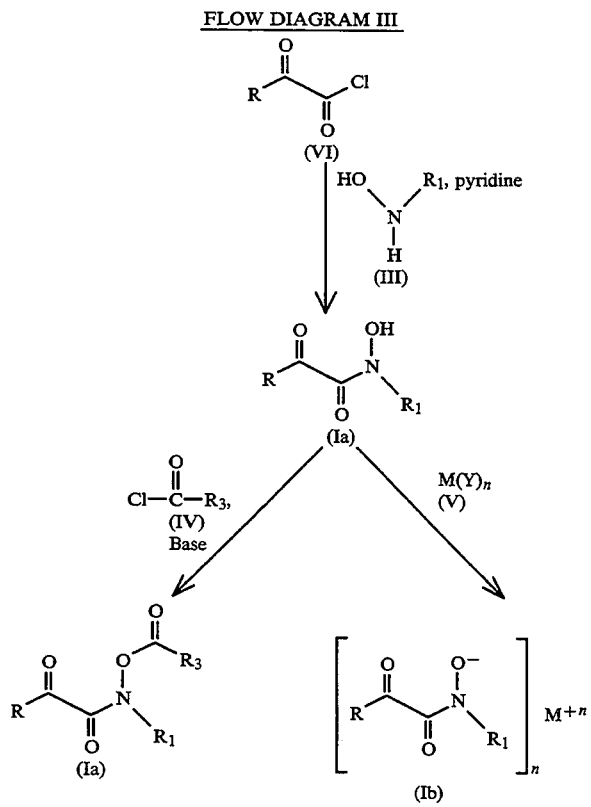

In Flow Diagram III, Y is $OC(O)CH_3$ or Cl and R, $R_1$, $R_3$, M and n are as described above.

As illustrated in Flow Diagram III, the appropriately substituted formula VI oxalic chloride may be reacted with a formula III hydroxylamine (or hydroxylamine hydrohalide salt) in the presence of pyridine to yield the formula Ia compound wherein $R_2$ is hydrogen. The formula Ia compound may then be reacted with an appropriate formula IV acid chloride to obtain those formula Ia compounds wherein $R_2$ is $COR_3$. Alternatively, the formula Ia compound wherein $R_2$ is hydrogen may be reacted with a formula V metal complex to give a chelate of formula Ib.

The hydroxamic compounds of the present invention are useful for controlling or preventing the growth of phytopathogenic fungi such as *Cercospora beticola, Venturia inaequalis, Alternaria solani, Mycosphaerella fijiensis, Cercospora arachidicola* and *Botrytis cinerea*. Therefore, harmful diseases such as sugar beet cercospora leaf spot, apple scab, tomato early blight, banana black sigatoka, peanut leaf spot, and grape and pepper botrytis may be prevented or controlled.

The compounds of the present invention are also useful for the protection of growing or harvested plants from the damage caused by phytopathogenic fungal disease when applied to said plants at a fungicidally effective rate. The effective rate will vary depending upon factors such as the virulence of the target fungus, the environment of the treatment and other ambient conditions. In practice, generally about 20 ppm to 1,000 ppm, preferably about 50 ppm to 500 ppm of the formula Ia or Ib compound may be dispersed in a liquid or solid carrier and applied to the plant, seed or tuber, or to the soil or water in which the plant, seed or tuber is growing.

The compounds of the invention may be formulated as concentrated solutions, emulsifiable concentrates, flowable concentrates, microemulsions and the like. Said compounds may also be formulated as dry compacted granules, granular compositions, dusts, dust concentrates, suspension concentrates, wettable powders, and the like. Those formulations which lend themselves to seed, tuber, soil, water and/or foliage applications to provide the requisite plant protection are suitable. Such formulations include the compounds of the invention admixed with an inert solid or liquid carrier.

It is contemplated that the compounds of the invention may be used in conjunction with, or in combination with, a pesticidally effective amount of one or more other pesticides, including but not limited to, anilazine, benalaxyl, benomyl, bitertanol, bordeaux mixture, carbendazim, carboxin, captafol, captan, chlorothalonil, cyproconazole, dichloran, diethofencarb, diniconazole, dithianon, dodine, edifenphos, fenarimol, fenbuconazole, fenfuram, fenpropidin, fenpropimorph, fentin hydroxide, ferbam, flusilazole, flusulfamide, flutriafol, folpet, fosetyl, fuberidazole, guazatine, hexaconazole, imazalil, iprobenfos, iprodione, mancozeb, maneb, metalaxyl, metiram, myclobutanil, nuarimol, ofurace, oxadixyl, oxycarboxin, penconazole, probenazole, prochloraz, propiconazole, pyrazophos, tebuconazole, thiabendazole, thiophanate, thiophanate-methyl, triadimefon, triadimenol, triarimol, tricyclazole, tridemorph, triflumizole, triforine, vinclozolin, zineb, and the like.

Where compositions of the invention are to be employed in combination treatments with other pesticidal agents, the composition may be applied concurrently as an admixture of the components as described above, or may be applied sequentially.

In order to facilitate a further understanding of the invention, the following examples are presented primarily for the purpose of illustrating more specific details thereof. The invention should not be deemed limited thereby except as defined in the appended claims.

EXAMPLE 1

Preparation of N-methyl-α-thio-1-adamantaneglyoxylohydroxamic acid

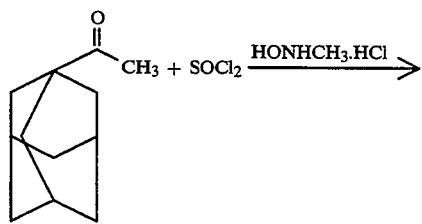

A mixture of 1-adamantyl methyl ketone (12.5 g, 0.07 mol), thionyl chloride and pyridine is refluxed for 2½ hours and concentrated with toluene in vacuo, to give a residue. The residue is dissolved in methylene chloride, filtered through a silica gel plug and concentrated in vacuo to give a red oil residue. The red oil is diluted with tetrahydrofuran and added to a mixture of N-methylhydroxylamine hydrochloride (12.5 g, 0.15 mol) and pyridine which has been heated at reflux temperature for 5 minutes and cooled. The resultant reaction mixture is stirred at 20° C. for 5 minutes, heated at reflux temperature for 45 minutes, cooled to room temperature and concentrated in vacuo to give a residue. The residue is dispersed in a mixture of ether and aqueous 10% hydrochloric acid. The phases are separated and the organic phase is extracted with 5% sodium carbonate. The carbonate extracts are combined and acidified with 10% hydrochloric acid to about pH 1, stirred for 1 hour and filtered. The filtercake is dried and recrystallized from heptane/ethyl acetate to give the title product as a white solid, mp 127°–141° C., identified by $^1$HNMR analysis.

Using essentially the same procedure, but employing the appropriately substituted methyl ketone substrate and a suitable hydroxylamine hydrochloride, the following compounds are obtained:

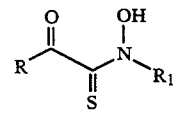

| R | R$_1$ | mp °C. |
|---|---|---|
| C(CH$_3$)$_3$ | CH$_3$ | 76–79 |
| C(CH$_3$)$_3$ | cyclopentyl | red oil |
| C(CH$_3$)$_3$ | CH(CH$_3$)$_2$ | |
| 1-methylcyclopropane | CH$_3$ | brown solid |
| C(CH$_3$)$_3$ | CH$_2$C$_6$H$_5$ | red oil |

EXAMPLE 2

Preparation of N-isopropyl-3,3-dimethyl-2-oxo-1-thiobutyrohydroxamic acid zinc (+2) chelate

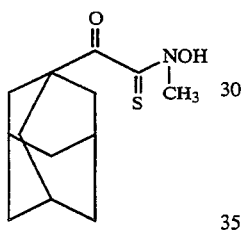

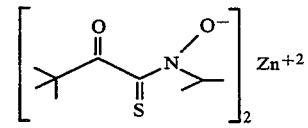

A mixture of N-isopropyl-3,3-dimethyl-2-oxo-1-thiobutyrohydroxamic acid (0.5 g, 2.5 mmol) and zinc diacetate dihydrate (0.25 g, 1.1 mmol) in acetic acid is heated at reflux temperature for 1 hour and concentrated in vacuo to give a residue. The residue is diluted with ether, washed sequentially with dilute sodium bicarbonate and brine. The organic phase is dried over MgSO$_4$ and concentrated in vacuo to give the title product as an off-white solid, mp 133°–140° C.

Using essentially the same procedure, and employing the appropriately substituted hydroxamic acid and metal diacetate, the following compounds are obtained:

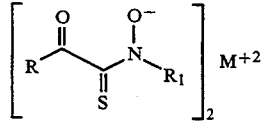

| R | R$_1$ | M | mp °C. |
|---|---|---|---|
| C(CH$_3$)$_3$ | CH$_2$C$_6$H$_5$ | Zn | 200–203 |
| C(CH$_3$)$_3$ | cyclopentyl | Zn | 140–146 |
| 1-adamantyl | CH$_3$ | Zn | 225 |
| C(CH$_3$)$_3$ | CH$_3$ | Zn | 158–159 |
| C(CH$_3$)$_3$ | CH$_2$C$_6$H$_5$ | Cu | red solid |
| C(CH$_3$)$_3$ | cyclopentyl | Cu | >225 |
| 1-adamantyl | CH$_3$ | Cu | >230 |
| C(CH$_3$)$_3$ | CH$_3$ | Cu | 153 dec. |
| C(CH$_3$)$_3$ | CH$_3$ | Mn | >255 |

EXAMPLE 3

Preparation of N,
3,3-trimethyl-2-oxo-1-thiobutyrohydroxamic acid iron
(+3) chelate

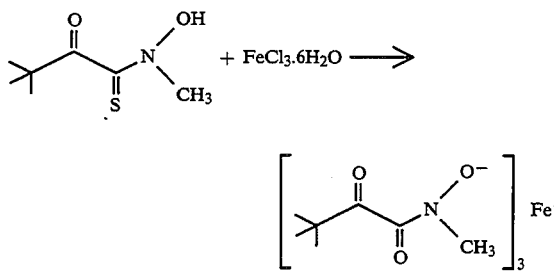

A solution of ferric chloride hexahydrate (376.4 mg, 1.39 mmol) in water is added to a solution of N,3,3-trimethyl-2-oxo-1-thiobutyrohydroxamic acid (750 mg, 4.22 mmol) in acetic acid. After the addition is complete, the reaction mixture is concentrated in vacuo and chased with toluene to give a black oil. The oil is crystallized from heptane to give the title product as a red-black solid (0.7 g, mp 144° C. dec.).

Using essentially the same procedure, but employing N-cyclopentyl-3,3-dimethyl-2-oxo-1-thiobutyrohydroxamic acid as the starting material, N-cyclopentyl-3,3-dimethyl-2-oxo-1-thiobutyrohydroxamic acid iron(+3) chelate is obtained as a dark red solid, mp 140°–146° C.

EXAMPLE 4

Preparation of p-Chlorobenzoate ester of
N,3,3-trimethyl-2-oxo-1-thiobutyrohydroxamate

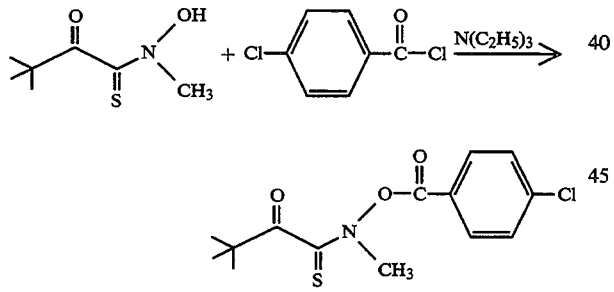

A mixture of triethylamine (1.6 mL) in methylene chloride is added dropwise to a mixture of N,3,3-trimethyl-2-oxo-1-thiobutyrohydroxamic acid (1.6 g, 9.13 mmol) and p-chlorobenzoyl chloride (1.3 mL, 10.04 mmol) in methylene chloride at about 5° C. When the addition is complete, the reaction mixture is diluted with methylene chloride, washed sequentially with 2% hydrochloric acid, 5% sodium carbonate solution and brine, dried over $Na_2SO_4$ and concentrated in vacuo to obtain a yellow oil. The oil is chromatographed using silica gel and a (10:1) hexane/ether as eluent to give the title product as a yellow solid, 2.4 g, mp 154°–162° C.

Using essentially the same procedure, but substituting acryloyl chloride and methyl chloroformate for p-chlorobenzoyl chloride, the acrylate ester of N,3,3-trimethyl-2-oxo-1-thiobutyrohydroxamate and methyl- carbonate ester of N,3,3-trimethyl-2-oxo-1thiobutyrohydroxamate are obtained.

EXAMPLE 5

Preparation of acetate ester of
N,3,3-trimethyl-2oxo-1-thiobutyrohydroxamate

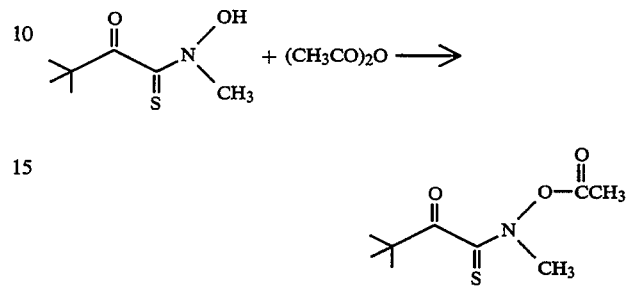

A solution of N,3,3-trimethyl-2-oxo-1-thiobutyrohydroxamic acid (1.75 g, 10 mmol) in pyridine is treated with acetic anhydride (1.13 mL, 12 mmol), stirred at room temperature for 1 hour and concentrated in vacuo to give a residue. The residue is diluted with ethyl acetate, washed sequentially with 10% hydrochloric acid, water, 5% sodium carbonate solution and brine, dried over $Na_2SO_4$ and concentrated in vacuo to give a yellow oil. The oil is crystallized from heptane to give the title product as a solid, 0.9 g, mp 82°–84° C.

EXAMPLE 6

Preparation of Carbanilate ester of
N-benzyl-3,3-dimethyl-2-oxo-1-thiobutyrohydroxamate

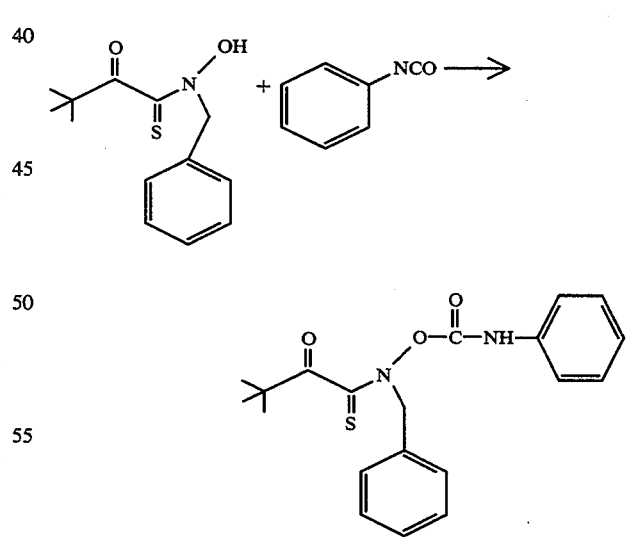

A mixture of phenyl isocyanate (0.47 g, 3.9 mmol) in ether is added to a solution of N-benzyl-3,3-dimethyl-2-oxo-1-thiobutyrohydroxamic acid (1.0 g, 3.9 mmol) in ether, stirred at room temperature for 5 to 10 minutes, concentrated in vacuo, to give a residue. The residue is diluted with heptane, stirred and filtered to give the title product as a solid, mp 119°–125° C.

EXAMPLE 7

Evaluation of In Vivo Fungicidal Activity of Test Compounds

Test compounds are dissolved or suspended in acetone and diluted with deionized water containing about 0.05% TWEEN 20®, a polyoxyethylene sorbitan monolaurate surfactant manufactured by Atlas Chemical Industries, to give a concentration of 200 ppm. Subsequent dilutions are made with an 0.05% aqueous solution of TWEEN 20®.

Host plants are sprayed with the test solution, dried and inoculated with fungi. When disease symptom development is optimal, the plants are rated for disease control according to the rating scale shown below. Each test contains inoculated treated plants, inoculated untreated plants and a reference standard. When more than one test is run, the data are averaged. The data obtained are shown in Table I.

| RATING SCALE | |
|---|---|
| Rating | Range % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| — | no evaluation |

| PHYTOPATHOGENIC FUNGI | | |
|---|---|---|
| Symbol | Disease | Pathogen |
| AS | Apple Scab | Venturia inaequalis |
| GDM | Grape Downy Mildew | Plasmopara viticola |
| PB | Pepper Botrytis | Botrytis cinerea |
| RB | Rice Blast | Pyricularia oryzae |
| SBC | Sugar Beet Cercospora | Cercospora beticola |
| TEB | Tomato Early Blight | Alternaria solani |
| WLR | Wheat Leaf Rust | Puccinia recondita f. sp. tritici |
| WPM | Wheat Powdery Mildew | Erysiphe graminis f. sp. tritici |
| RSB | Rice Sheath Blight | Rhizoctonia solani |
| PCE | Peanut Cercospora Early Leaf Spot | Cercospora arachidicola |
| WES | Wheat Eyespot | Pseudocercosporella herpotrichoides |

TABLE I

In Vivo Fungicidal Evaluations

| Compound | Rate (ppm) | AS | GDM | PB | RB | SBC | TEB | WLR | WPM | RSB | PCE | WES |
|---|---|---|---|---|---|---|---|---|---|---|---|---|
| N,3,3-trimethyl-2-oxo-1-thiobutyrohydroxamic acid | 200 | 5.0 | 4.3 | 3.0 | 2.7 | 7.0 | 2.7 | 1.7 | 6.3 | — | — | — |
|  | 400 | — | — | — | — | 3.5 | — | — | — | 0.3 | — | — |
| N,3,3-trimethyl-2-oxo-1-thiobutyrohydroxamic acid zinc(+2) chelate | 200 | 9.0 | 9.0 | 8.5 | 8.0 | 8.4 | 8.5 | 7.5 | 3.0 | — | — | — |
|  | 400 | — | — | — | — | 7.5 | — | — | — | 6.0 | — | — |
| N,3,3-trimethyl-2-oxo-1-thiobutyrohydroxamic acid iron(+3) chelate | 200 | 9.0 | 8.5 | 6.0 | 0.0 | 8.2 | 9.0 | 6.5 | 5.5 | — | — | — |
|  | 400 | — | — | — | — | 6.8 | — | — | — | 3.3 | — | — |
| N,3,3-trimethyl-2-oxo-1-thiobutyrohydroxamic acid copper(+2) chelate | 200 | 8.0 | 7.7 | 6.5 | 0.0 | 7.2 | 9.0 | 6.5 | 5.0 | — | — | — |
|  | 400 | — | — | — | — | 6.1 | — | — | — | 4.7 | 7.0 | 6.7 |
| N,3,3-trimethyl-2-oxo-1-thiobutyrohydroxamic acid manganese(+2) chelate | 200 | 8.5 | 5.5 | 8.5 | 3.0 | 7.5 | 8.5 | 6.5 | 7.0 | — | — | — |
|  | 400 | — | — | — | — | — | — | — | — | 0.0 | — | — |
| N-methyl-alpha-thio-1-adamantaneglyoxylohydroxamic acid | 200 | 0.0 | 0.0 | 0.0 | 0.0 | 1.8 | 0.0 | — | 0.0 | — | — | — |
|  | 400 | — | — | — | — | 3.0 | — | — | — | — | — | — |
| N-methyl-alpha-thio-1-adamantaneglyoxylohydroxamic acid zinc(+2) chelate | 200 | 0.0 | 0.0 | 0.0 | 0.0 | 0.5 | 0.0 | — | 0.0 | — | — | — |
|  | 400 | — | — | — | — | 3.0 | — | — | — | — | — | — |
| N-methyl-alpha-thio-1-adamantaneglyoxylohydroxamic acid copper(+2) chelate | 200 | 0.0 | 0.0 | 0.0 | 0.0 | 0.5 | 0.0 | — | 0.0 | — | — | — |
|  | 400 | — | — | — | — | 1.8 | — | — | — | — | — | — |
| N-cyclopentyl-3,3-dimethyl-2-oxo-1-thiobutyrohydroxamic acid | 200 | 0.0 | 0.0 | 0.0 | 0.0 | 0.3 | 0.0 | — | 0.0 | — | — | — |
| N-cyclopentyl-3,3-dimethyl-2-oxo-1-thiobutyrohydroxamic acid iron(+3) chelate | 200 | 0.0 | 0.0 | 0.0 | 0.0 | 0.8 | 0.0 | — | 0.0 | — | — | — |
|  | 400 | — | — | — | — | 1.8 | — | — | — | — | — | — |
| N-cyclopentyl-3,3-dimethyl-2-oxo-1-thiobutyrohydroxamic acid zinc(+2) chelate | 200 | 0.0 | 0.0 | 0.0 | 0.0 | 2.3 | 0.0 | — | 0.0 | — | — | — |
|  | 400 | — | — | — | — | 1.0 | — | — | — | — | — | — |
| N-cyclopentyl-3,3-dimethyl-2-oxo-1-thiobutyrohydroxamic acid copper(+2) chelate | 200 | 0.0 | 0.0 | 0.0 | 0.0 | 0.5 | 0.0 | — | 0.0 | — | — | — |
|  | 400 | — | — | — | — | 2.0 | — | — | — | — | — | — |
| N-isopropyl-3,3-dimethyl-2-oxo-1-thiobutyrohydroxamic acid zinc(+2) chelate | 200 | 0.0 | 3.0 | 2.0 | 0.0 | 0.0 | 0.0 | — | 0.0 | — | — | — |
| N-benzyl-3,3-dimethyl-2-oxo-1-thiobutyrohydroxamic acid zinc(+2) chelate | 200 | 0.0 | 0.0 | 0.0 | 0.0 | 6.0 | 0.0 | — | 0.0 | — | — | — |
| Acetate ester of N,3,3- | 200 | 0.0 | 0.0 | 0.0 | 0.0 | 0.0 | 5.0 | — | 0.0 | — | — | — |

TABLE I-continued

| | | In Vivo Fungicidal Evaluations | | | | | | | | | | |
|---|---|---|---|---|---|---|---|---|---|---|---|---|
| Compound | Rate (ppm) | AS | GDM | PB | RB | SBC | TEB | WLR | WPM | RSB | PCE | WES |
| trimethyl-2-oxo-1-thio-butyrohydroxamate | | | | | | | | | | | | |
| Acrylate ester of N,3,3-trimethyl-2-oxo-1-thio-butyrohydroxamate | 200 | 0.0 | 0.0 | 2.0 | 0.0 | 0.0 | 0.0 | — | 0.0 | — | — | — |
| Methylcarbonate ester of N,3,3-trimethyl-2-oxo-1-thiobutyrohydroxamate | 200 | 0.0 | 0.0 | 0.0 | 0.0 | 0.0 | 2.0 | — | 0.0 | — | — | — |
| p-Chlorobenzoate ester of N,3,3-trimethyl-2-oxo-1-thiobutyrohydroxamate | 200 | 8.0 | 0.0 | 8.0 | 6.0 | 4.0 | 6.0 | — | 3.0 | — | — | — |

EXAMPLE 8

Evaluation of In Vitro Fungicidal Activity of Test Compounds

Test compounds are dissolved in acetone and dispersed into cell well plates containing a suspension of ground fungal mycelia in a nutrient broth. Assay plates are incubated for 3–4 days at 21° C. Growth inhibition is measured visually and is rated using the following scale:

| Rating | % Inhibition |
|---|---|
| 0 | 0 |
| 1 | 1–29 |
| 3 | 30–59 |
| 5 | 60–89 |
| 7 | 90–99 |
| 9 | 100 |

Untreated controls, solvent blanks and reference standards are included in each test.

Assay fungi include the plant pathogens, *Pythium ultimum* (Pythul); *Rhizoctonia solani* (Rhizso); *Fusarium oxysporum f. sp. cucumerinum* (Fusoxc); and *Pseudocercosporella herpotrichoides* (Psdche).

When more than one test is run, the data are averaged. The data obtained are shown in Table II.

TABLE II

| | | In Vitro Fungicidal Evaluations | | | |
|---|---|---|---|---|---|
| Compound | Rate (ppm) | FUSOXC | PSDCHE | PYTHUL | RHIZSO |
| N,3,3-trimethyl-2-oxo-1-thiobutyrohydroxamic acid | 25 | 0.0 | 1.0 | 6.0 | 6.0 |
| N,3,3-trimethyl-2-oxo-1-thiobutyrohydroxamic acid zinc(+2) chelate | 25 | 4.5 | 4.0 | 8.5 | 4.5 |
| N,3,3-trimethyl-2-oxo-1-thiobutyrohydroxamic acid iron(+3) chelate | 25 | 1.3 | 2.5 | 8.0 | 4.5 |
| N,3,3-trimethyl-2-oxo-1-thiobutyrohydroxamic acid copper(+2) chelate | 25 | 4.8 | 8.5 | 8.0 | 8.5 |
| N,3,3-trimethyl-2-oxo-1-thiobutyrohydroxamic acid manganese(+2) chelate | 25 | 0.0 | 7.0 | 6.0 | 4.5 |
| N-methyl-2-alpha-thio-1-adamantaneglyoxylohydroxamic acid | 25 | 1.7 | 3.3 | 7.0 | 1.0 |
| N-methyl-alpha-thio-1-adamantaneglyoxylohydroxamic acid zinc(+2) chelate | 25 | 0.0 | 0.0 | 1.5 | 0.0 |
| N-methyl-alpha-thio-1-adamantaneglyoxylohydroxamic acid copper(+2) chelate | 25 | 0.0 | 0.0 | 0.0 | 0.0 |
| N-cyclopentyl-3,3-dimethyl-2-oxo-1-thiobutyrohydroxamic acid | 25 | 1.5 | 1.5 | 3.0 | 1.5 |
| N-cyclopentyl-3,3-dimethyl-2-oxo-1-thiobutyrohydroxamic acid iron(+3) chelate | 25 | 0.0 | 0.0 | 0.0 | 0.0 |
| N-cyclopentyl-3,3-dimethyl-2-oxo-1-thiobutyrohydroxamic acid zinc(+2) chelate | 25 | 3.7 | 3.0 | 7.0 | 3.3 |
| N-cyclopentyl-3,3-dimethyl-2-oxo-1-thiobutyrohydroxamic acid copper(+2) chelate | 25 | 0.0 | 0.0 | 0.0 | 0.0 |
| N-benzyl-3,3-dimethyl-2-oxo-1-thiobutyrohydroxamic acid | 25 | 3.5 | 7.0 | 7.0 | 4.5 |
| Carbanilate ester of N-benzyl-3,3-dimethyl-2-oxo-1- | 25 | 0.5 | 0.0 | 6.0 | 2.5 |

TABLE II-continued

| | | In Vitro Fungicidal Evaluations | | | |
|---|---|---|---|---|---|
| Compound | Rate (ppm) | FUSOXC | PSDCHE | PYTHUL | RHIZSO |
| thiobutyrohydroxamate | | | | | |
| N,1-dimethyl-alpha-thio-cyclopropaneglyoxylohydroxamic acid | 25 | 0.5 | 0.0 | 7.0 | 0.0 |
| N-benzyl-3,3-dimethyl-2-oxo-1-thiobutyrohydroxamic acid copper(+2) chelate | 25 | 0.0 | 0.0 | 1.5 | 1.5 |
| N-isopropyl-3,3-dimethyl-2-oxo-1-thiobutyrohydroxamic acid zinc(+2) chelate | 25 | 2.7 | 0.0 | 6.3 | 1.0 |
| N-benzyl-3,3-dimethyl-2-oxo-1-thiobutyrohydroxamic acid zinc(+2) chelate | 25 | 0.0 | 0.0 | 4.0 | 0.0 |
| Acetate ester of N,3,3-trimethyl-2-oxo-1-thiobutyrohydroxamate | 25 | 0.0 | 0.0 | 9.0 | 0.0 |
| Acrylate ester of N,3,3-trimethyl-2-oxo-1-thiobutyrohydroxamate | 25 | 0.0 | 7.0 | 9.0 | 0.0 |
| Methylcarbonate ester of N,3,3-trimethyl-2-oxo-1-thiobutyrohydroxamate | 25 | 0.0 | 0.0 | 5.0 | 0.0 |
| p-Chlorobenzoate ester of N,3,3-trimethyl-2-oxo-1-thiobutyrohydroxamate | 25 | 0.0 | 0.0 | 0.0 | 0.0 |

EXAMPLE 9

Evaluation of Test Compounds for the Control of Banana Black Sigatoka

Test compounds are dissolved in acetone and diluted with distilled water containing about 0.05% TWEEN 20 ® to give a concentration of 200 ppm.

Banana seedlings at the 6-7 leaf stage are sprayed with test solution on the upper and lower surfaces of the 3 youngest, unfurled leaves to the point of run-off, dried and inoculated with a spore suspension of *Mycosphaerella fijiensis*. The inoculated banana seedlings are placed outdoors in a plastic tunnel lined with wet jute sacks. The temperature is maintained between about 25° and 32° C. and the relative humidity is maintained between about 85% and 100%. After five days, the banana seedlings are transferred to a partially shaded screenhouse, surrounded with wet jute sacks and misted daily. When disease symptom development is optimal, typically 28 to 40 days post inoculation, the banana seedlings are rated for disease control according to the rating scale shown below. Each test contains inoculated treated plants, inoculated untreated plants and a reference standard.

When more than one test is run, the data are averaged. The data obtained are shown in Table III.

| Rating Scale | |
|---|---|
| Rating | Range % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

TABLE III

| Evaluation Of Test Compounds For The Control Of Banana Black Sigatoka | |
|---|---|
| Compound | Control of Banana Black Sigatoka |
| N,3,3-trimethyl-2-oxo-1-thiobutyrohydroxamic acid | 3.7 |
| N,3,3-trimethyl-2-oxo-1-thiobutyrohydroxamic acid copper(+2) chelate | 6.3 |

EXAMPLE 10

Evaluation of Test Compounds for the Control of Soil Borne Diseases

Pasturized soil (100 mL) is added to 6 cm diameter plastic cups without drainage holes and covered with pathogen contaminated soil (30 mL). Ten germinated cucumber seeds are planted on the contaminated soil and the seeds are covered with pasteurized soil (20 mL). Test compounds are dissolved in acetone, diluted with deionized water containing about 0.05% TWEEN 20 ®, and applied to the pots by drenching the soil surface with 15 mL of test solution. The pots are placed in a greenhouse for disease development. The pots are watered lightly until plants emerge from the soil surface. Disease evaluations are made 14–18 days after treatment according to the rating scale shown below. The data obtained are shown in Table IV.

| RATING SCALE | |
|---|---|
| Rating | Range % Control |
| 0 | 0 |

-continued

RATING SCALE

| Rating | Range % Control |
|---|---|
| 1 | 5–10 |
| 2 | 15–25 |
| 3 | 30–40 |
| 4 | 45–55 |
| 5 | 60–70 |
| 6 | 75–85 |
| 7 | 90 |
| 8 | 95 |
| 9 | 100 |

FUNGI

| Symbol | Disease | Pathogen |
|---|---|---|
| CURS | Cucumber damping-off by Rhizoctonia | *Rhizoctonia solani* |
| CUPA | Cucumber damping-off by Pythium | *Pythium aphanidermantum* |
| CUFO | Cucumber Fusarium Wilt | *Fusarium oxysporum f. sp. cucumerinum* |

TABLE IV

Evaluation of Test Compounds Against Soil Diseases

| Compound | Rate (kg/ha) | CUFO | CUPA | CURS |
|---|---|---|---|---|
| N,3,3-trimethyl-2-oxo-1-thiobutyrohydroxamic acid | 10.0 | 1 | 3 | 7 |
|  | 5.0 | 0 | 2 | 5 |
|  | 2.5 | 1 | 2 | 2 |
| N,3,3-trimethyl-2-oxo-1-thiobutyrohydroxamic acid zinc(+2) chelate | 10.0 | 4 | 4 | 9 |
|  | 5.0 | 1 | 2 | 6 |
|  | 2.5 | 2 | 0 | 4 |
| N,3,3-trimethyl-2-oxo-1-thiobutyrohydroxamic acid iron(+3) chelate | 10.0 | 3 | 2 | 9 |
|  | 5.0 | 2 | 1 | 6 |
|  | 2.5 | 1 | 0 | 4 |
| N,3,3-trimethyl-2-oxo-1-thiobutyrohydroxamic acid copper(+2) chelate | 10.0 | 6 | 1 | 9 |
|  | 5.0 | 5 | 2 | 6 |
|  | 2.5 | 3 | 1 | 5 |

I claim:

1. A compound having the structural formula

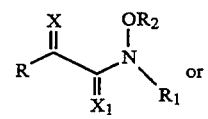

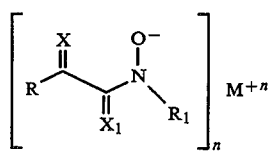

wherein
X and $X_1$ are each independently O or S;
R is $C_1$–$C_6$ alkyl optionally substituted with one or more halogen atoms, or
$C_3$–$C_{12}$ cycloalkyl or polycycloalkyl optionally substituted with one or more $C_1$–$C_4$ alkyl groups;
$R_1$ is $C_3$–$C_8$ cycloalkyl,
$C_1$–$C_8$ alkyl optionally substituted with one or more halogen atoms,
benzyl optionally substituted with one or more halogen, CN, $NO_2$, $C_1$–$C_4$ alkyl or $C_1$–$C_4$ haloalkyl groups;
phenyl optionally substituted with one or more halogen, CN, $NO_2$, $C_1$–$C_4$ alkyl or $C_1$–$C_4$ haloalkyl groups;
$R_2$ is hydrogen or

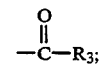

$R_3$ is hydrogen,
$OR_4$,
$NR_5R_6$,
$C_1$–$C_6$ alkyl optionally substituted with one or more halogen atoms,
$C_3$–$C_8$ cycloalkyl optionally substituted with one or more halogen atoms,
$C_2$–$C_6$ alkenyl optionally substituted with one or more halogen atoms, or
phenyl optionally substituted with one or more halogen, CN, $NO_2$, $C_1$–$C_4$ alkyl, $C_1$–$C_4$ alkoxy or $C_1$–$C_4$ haloalkyl groups;
$R_4$ is $C_1$–$C_6$ alkyl;
$R_5$ and $R_6$ are each independently hydrogen, $C_1$–$C_6$ alkyl, or phenyl optionally substituted with one or more halogen, CN, $NO_2$, $C_1$–$C_4$ alkyl or $C_1$–$C_4$ haloalkyl groups;
n is an integer of 1, 2, 3 or 4; and
M is an alkali metal, an alkaline earth metal, a transition metal other than one selected from the lanthanides, boron or aluminum.

2. The compound according to claim 1 wherein
X is O;
$X_1$ is S;
R is $C_1$–$C_6$ alkyl;
$R_1$ is $C_1$–$C_8$ alkyl;
$R_2$ is hydrogen or

$R_3$ is phenyl optionally substituted with one or more halogen, CN, $NO_2$, $C_1$–$C_4$ alkyl, $C_1$–$C_4$ alkoxy or $C_1$–$C_4$ haloalkyl groups;
n is an integer of 2 or 3; and
M is iron, zinc or copper.

3. The compound according to claim 2, N,3,3-trimethyl-2-oxo-1-thiobutyrohydroxamic acid iron(+3) chelate.

4. The compound according to claim 2, N,3,3-trimethyl-2-oxo-1-thiobutyrohydroxamic acid copper(+2) chelate.

5. The compound according to claim 2, N,3,3-trimethyl-2-oxo-1-thiobutyrohydroxamic acid zinc(+2) chelate.

6. The compound according to claim 2, p-chlorobenzoate ester of N,3,3-trimethyl-2-oxo-1-thiobutyrohydroxamate.

7. A method for the prevention, control or amelioration of a disease caused by a phytopathogenic fungus which comprises contacting said fungus with a fungicidally effective amount of a compound having the structure

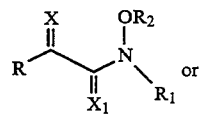

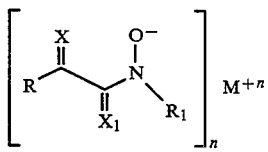

wherein X, $X_1$, R, $R_1$, $R_2$, M and n are described in claim 1.

8. The method according to claim 7 wherein
X is O;
$X_1$ is S;
R is $C_1$–$C_6$ alkyl;
$R_1$ is $C_1$–$C_8$ alkyl;
$R_2$ is hydrogen or

$R_3$ is phenyl optionally substituted with one or more halogen, CN, $NO_2$, $C_1$–$C_4$ alkyl, $C_1$–$C_4$ alkoxy or $C_1$–$C_4$ haloalkyl groups;
n is an integer of 2 or 3; and
M is iron, zinc or copper.

9. The method according to claim 8 wherein the compound is selected from the group consisting of
N,3,3-trimethyl-2-oxo-1-thiobutyrohydroxamic acid iron(+3) chelate;
N,3,3-trimethyl-2-oxo-1-thiobutyrohydroxamic acid copper(+2) chelate;
N,3,3-trimethyl-2-oxo-1-thiobutyrohydroxamic acid zinc(+2) chelate; and
p-chlorobenzoate ester of N,3,3-trimethyl-2-oxo-1-thiobutyrohydroxamate.

10. The method according to claim 7 wherein the compound is applied at a concentration of about 20 ppm to 1,000 ppm.

11. The method according to claim 8 wherein the disease is sugar beet cercospora leaf spot.

12. The method according to claim 8, further comprising the concurrent or sequential application of a pesticidally effective amount of one or more other pesticidal agents.

13. A method for the protection of a plant, plant seed or tuber from fungal infestation and disease which comprises applying to the plant, plant seed or tuber, or to the soil or water in which it is growing, a fungicidally effective amount of a compound having the structure

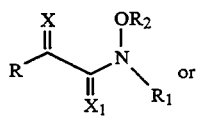

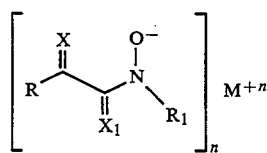

wherein X, $X_1$, R, $R_1$, $R_2$, M and n are described in claim 1.

14. The method according to claim 13 wherein
X is O;
$X_1$ is S;
R is $C_1$–$C_6$ alkyl;
$R_1$ is $C_1$–$C_8$ alkyl;
$R_2$ is hydrogen or

$R_3$ is phenyl optionally substituted with one or more halogen, CN, $NO_2$, $C_1$–$C_4$ alkyl, $C_1$–$C_4$ alkoxy or $C_1$–$C_4$ haloalkyl groups;
n is an integer of 2 or 3; and
M is iron, zinc or copper.

15. The method according to claim 14 wherein the compound is selected from the group consisting of
N,3,3-trimethyl-2-oxo-1-thiobutyrohydroxamic acid iron(+3) chelate;
N,3,3-trimethyl-2-oxo-1-thiobutyrohydroxamic acid copper(+2) chelate;
N,3,3-trimethyl-2-oxo-1-thiobutyrohydroxamic acid zinc(+2) chelate; and
p-chlorobenzoate ester of N,3,3-trimethyl-2-oxo-1-thiobutyrohydroxamate.

16. The method according to claim 14 wherein the fungal infestation and disease is sugar beet cercospora leaf spot.

17. A composition for controlling phytopathogenic fungi which comprises an inert liquid or solid carrier and a fungicidally effective amount of a compound having the structure

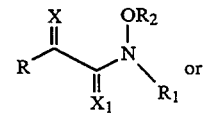

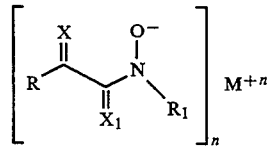

wherein X, $X_1$, R, $R_1$, $R_2$, M and n are described in claim 1.

18. The composition according to claim 17 wherein
X is O;
$X_1$ is S;
R is $C_1$–$C_6$ alkyl;
$R_1$ is $C_1$–$C_8$ alkyl;
$R_2$ is hydrogen or

$R_3$ is phenyl optionally substituted with one or more halogen, CN, $NO_2$, $C_1$-$C_4$ alkyl, $C_1$-$C_4$ alkoxy or $C_1$-$C_4$ haloalkyl groups;

n is an integer of 2 or 3; and

M is iron, zinc or copper.

19. The composition according to claim 18 wherein the phytopathogenic fungi is *Cercospora beticola.*

20. The composition according to claim 17, further comprising a pesticidally effective amount of one or more other pesticidal agents.

* * * * *